United States Patent [19]

Haney

[11] Patent Number: 4,463,598

[45] Date of Patent: Aug. 7, 1984

[54] CAPILLARY BRIDGE VISCOMETER

[76] Inventor: Max A. Haney, 1030 Russell Dr., Porter, Tex. 77365

[21] Appl. No.: 448,525

[22] Filed: Dec. 10, 1982

[51] Int. Cl.$^3$ ............................................. G01N 11/04
[52] U.S. Cl. ..................................... 73/55; 73/61.1 C
[58] Field of Search .......................... 73/54, 55, 61.1 C

[56] References Cited

U.S. PATENT DOCUMENTS 3,086,386  4/1963  Kapff ........................................ 73/54
3,808,877  5/1974  Blair ......................................... 73/55
3,962,907  6/1976  Peyrouset et al. ....................... 73/55

FOREIGN PATENT DOCUMENTS 805120  2/1981  U.S.S.R. .................................... 73/54

OTHER PUBLICATIONS

A. D. Sotskov, Detecting Liquid Binary Solutions on the Basis of Differences in Partial Viscosities, 7/1975.

*Primary Examiner*—Gerald Goldberg
*Assistant Examiner*—Hezron Williams
*Attorney, Agent, or Firm*—Richard L. Kelly

[57] ABSTRACT

A capillary bridge viscometer is disclosed for measuring the relative viscosity of a solute in a solvent. The bridge contains two (2) fluid flow circuits. One circuit contains two (2) capillaries in series. The second circuit contains two (2) capillaries in series with a valve and an associated liquid reservoir positioned intermediate of the capillaries. A common feed line feeds a first liquid to both fluid flow circuits. With the valve set in one operating position, the first liquid flows through all four (4) capillaries and no pressure differential is established across the bridge. With the valve set in a second operating position, the first liquid exiting the first capillary of the second fluid flow circuit flows into the liquid reservoir and displaces a second liquid stored therein which then flows through the second capillary of the second fluid flow circuit. A differential pressure is established across the bridge which is a function of the viscosity of the second liquid.

18 Claims, 6 Drawing Figures

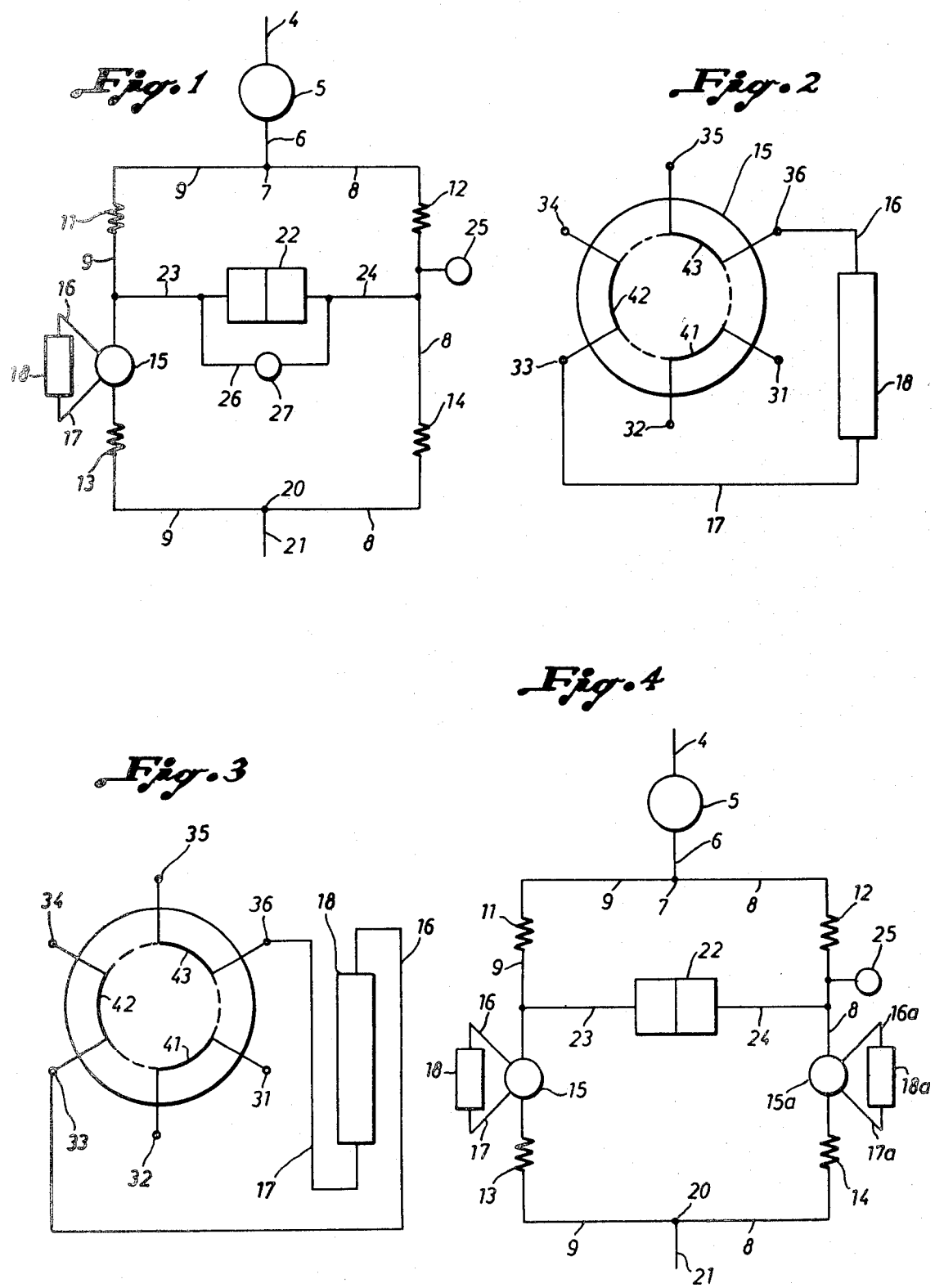

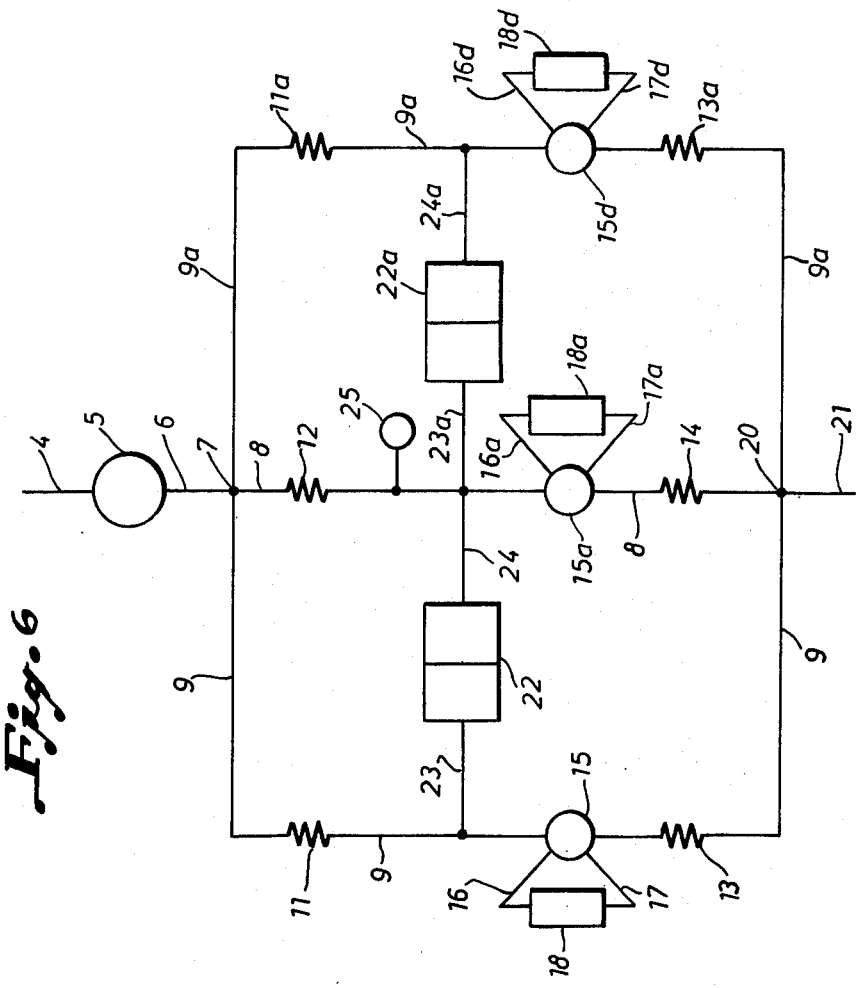
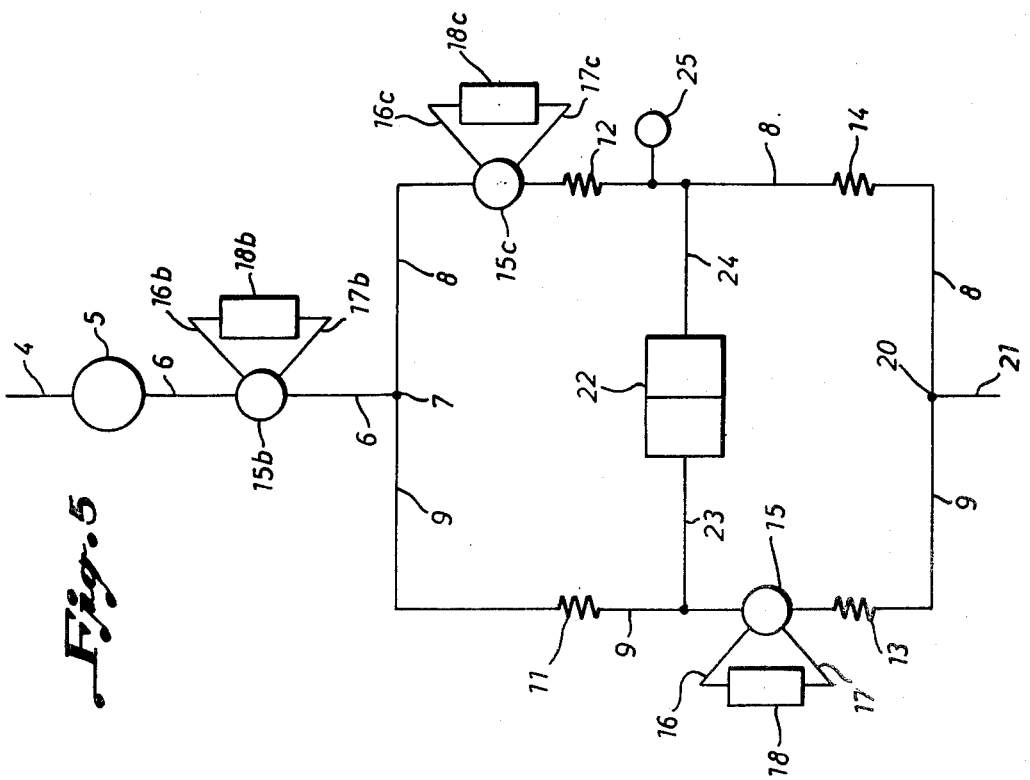

CAPILLARY BRIDGE VISCOMETER

BACKGROUND OF THE INVENTION

1. Field of the Invention

The invention relates to capillary bridge viscometers useful for measuring the relative viscosity of a solute in solution with a solvent for said solute.

2. The Prior Art

A common method employed to obtain information respecting molecular weights of solvent soluble thermoplastic polymers is to measure the viscosity of dilute solutions of such polymers in a suitable solvent. From the knowledge of the viscosity of such dilute solution and the known viscosity of the solvent employed in such determinations, it is possible to obtain data respecting the relative viscosity, specific viscosity, and inherent viscosity of such thermoplastic polymers.

The usefulness of methods for determining molecular weight of polymers by this method is limited by the quantity of work and the time required to obtain such data. Such data are customarily obtained by preparing the polymer solutions and measuring the viscosity of the solutions in carefully calibrated viscometers. To obtain data respecting intrinsic viscosity, it is necessary to measure relative viscosity a several concentrations and to extrapolate such data to zero concentration of the solute in the solvent.

It would be highly desirable to have available to the art apparatus for measuring such viscosities with a high level of precision in relatively short time periods. Notwithstanding the desirability of having such apparatus, the applicant is not aware of apparatus which will measure such viscosities conveniently and accurately in short periods of time.

SUMMARY OF THE INVENTION

Apparatus has been developed which has the capability of accurately measuring the viscosity of a dilute solution of a solute in a solvent therefor. The apparatus includes a bridge containing two fluid flow circuits. The first circuit includes a fluid line and includes therein, in series, two capillaries. The second fluid flow circuit is a fluid line which includes therein, in sequence in the fluid flow stream;

(a) a first capillary;
(b) a liquid reservoir having a liquid volume substantially larger than the volume of said first capillary, and including a liquid inlet and a liquid outlet in communication with the fluid line;
(c) a second capillary; and
(d) valving means which feed the liquid exiting the first capillary directly into the second capillary or into the liquid reservoir.

The apparatus includes a liquid inlet line which feeds both the first and second fluid flow circuits. Means are provided for measuring the gauge pressure in the viscometer at any point upstream of the second capillary in either the first or second fluid flow circuits. Finally, means are provided for measuring the differential pressure existing between;

(1) a point intermediate of the capillaries in the first fluid flow circuit, and
(2) a point intermediate of the capillaries in the second fluid flow circuit.

The lengths and diameters of the capillaries are selected so that essentially no pressure differential is established between the two fluid flow circuits when a common fluid is flowing through all of the capillaries.

BRIEF DESCRIPTION OF THE DRAWINGS

FIG. 1 illustrates one embodiment of the invention.
FIG. 2 illustrates one hookup of the valving means to the liquid reservoir.
FIG. 3 illustrates another hookup of the valving means to the liquid reservoir.
FIG. 4 illustrates a modification of the embodiment of FIG. 1 in which a liquid reservoir and associated valving means also are included in the first fluid flow circuit.
FIG. 5 illustrates a second modification of the embodiment of the invention illustrated in FIG. 1.
FIG. 6 illustrates another embodiment of the invention in which the viscosity of two polymer solutions can be determined simultaneously.

DETAILED DESCRIPTION OF THE INVENTION

Referring to FIG. 1, the apparatus includes a solvent reservoir 5 which is connected through line 6 to a junction point 7 in the bridge circuit. Line 4 is connected to a source of constant pressure gas such as nitrogen at 5–10 psi which drives the solvent from reservoir 5 through the bridge. The first fluid circuit includes a line 8 which runs from junction point 7 to junction point 20 and includes therein, in series, capillary 12 and capillary 14. The second fluid flow circuit includes a line 9 which runs from junction point 7 to junction point 20. Line 21 is connected to junction point 20 and discharges the fluid being fed through the bridge. The second fluid circuit includes, in sequence in the fluid flow stream, a first capillary 11, valving means 15, and a second capillary 13. A pressure gauge 25 is included in the bridge to measure gauge pressure. This gauge can be positioned at any point in line 6, 8, or 9, provided only that it is upstream from capillary 13 or capillary 14. A differential pressure transducer 22 is connected across the two fluid flow circuits of the bridge by lines 23 and 24 to measure the differential pressure developed across the bridge when two different fluids are flowing through the capillaries in the bridge as subsequently described in greater detail. A line 26 having a valve 27 therein is connected across lines 23 and 24. When the bridge is being first filled with fluid at start up, valve 27 is opened to equalize pressure across the bridge to protect transducer 22 from any sudden large pressure differences which could damage the transducer. Once the bridge is filled with fluid, valve 27 is closed. Similar protective lines and valves are used with the transducers in FIGS. 4, 5, and 6 but are not shown.

FIG. 2 illustrates the operation of valving means 15 and associated liquid reservoir 18 included in FIG. 1. Valving means 15 is a two-position 6-port valve of the type commercially available from commercial sources such as VALCO Instruments, Inc., of Houston, Tex. Liquid reservoir 18 is a vertically aligned wide-bore column which typically will have a 0.25" O.D., be about 1' long, and have an internal volume of about 4.0 ml.

Valve 15 has six (6) ports 31, 32, 33, 34, 35, and 36. Valve 15 also has three (3) internal arcuate lines 41, 42, and 43. In the valve's first operating position, line 41 connects to ports 31 and 32; line 42 connects to ports 33 and 34; and line 43 connects to ports 35 and 36. In the valve's second operating position, set by rotating the element containing lines 41, 42, and 43 counterclockwise through an arch of 60°, line 41 connects to ports 31 and 36; line 43 connects to ports 35 and 34; and line 42 connects to ports 33 and 32. In the second operating position lines 41, 42, 43 occupy the positions shown by the dotted lines in FIG. 2. Port 36 is connected by line 16 to the top of liquid reservoir 18. Port 33 is connected by line 17 to the bottom of liquid reservoir 18. Wherever subsequently used, the terms "first position" (or "first operating position") and "second position" (or "second operating position") will have the same meaning as discussed above.

To determine the relative viscosity of a solute dissolved in a solvent, valve means 15 is set in its first operating position in which line 41 connects to ports 31 and 32. Port 31 will be connected to receive fluid exiting capillary 11. Port 32 will be connected to feed fluid from valving means 15 to capillary 13. Liquid reservoir 18 will be loaded with the sample solution by injecting the sample through open port 34. The sample flows through arcuate line 42, exits port 33, flows through line 17, fills reservoir 18, flows through line 16, enters port 36, flows through arcuate line 43 and exits port 35 to a waste line (not shown).

A valve (not shown) in line 4 is opened to start a flow of solvent through the bridge. The solvent flows through the first circuit which includes line 8 and capillaries 12 and 14. The solvent flowing through the second circuit, after discharge from capillary 11, enters valving means 15 through port 31. The solvent flows through arcuate line 41 and exits via port 32. It then flows through capillary 13. Solvent from both circuits is discharged through line 21. Valve 27 is kept in an open position until the entire bridge is filled with solvent and solvent is discharged through line 21. Valve 27 then is closed. At this time, both circuits, including capillaries 11, 12, 13, and 14, are filled with solvent. The flow rate through both circuits is identical and no pressure differential is detected by the transducer 22.

The valving means 15 then is switched to its second operating position in which line 41 connects to ports 31 and 36. The solvent entering port 31 now flows through arcuate line 41, exits through port 36, and flows through line 16 into the top of liquid reservoir 18. By reason of the relatively larger diameter of the liquid reservoir, there is little or no viscous flow within the reservoir and the flow of liquid through the reservoir is essentially plug flow. Accordingly, the solvent entering the liquid reservoir displaces the sample solution contained therein. The displaced sample solution flows through line 17, valve port 33, arcuate line 42, and valve port 32 to enter line 9 and capillary 13.

As the sample solution flowing through capillary 13 has a greater viscosity than the solvent flowing through capillaries 11, 12, and 14, the pressure at any point intermediate of capillaries 11 and 13 is greater than the pressure at any point intermediate of capillaries 12 and 14. Accordingly, a differential pressure exists between the two circuits. The differential pressure is measured by transducer 22 and can be recorded on a suitable strip chart (not shown). The calculations employed to determine the solute's relative viscosity are discussed infra.

The valving means 15 then is switched back to its first operating position in which solvent flows through all of the capillaries. The liquid reservoir 18 then is filled with a second sample solution as previously described. The apparatus then is ready to measure the viscosity of the second sample.

As the pressure differentials to be measured are small, all of the fluid lines, the solvent reservoir, and the liquid reservoir will be insulated so that both fluids in the apparatus will be maintained at the same temperature. To assure plug flow through the liquid reservoir, the liquid reservoir will be mounted in a vertical plane. The other elements of the two fluid flow circuits can be mounted in either a vertical or horizontal plane.

FIG. 4 illustrates a modification of the embodiment of the invention illustrated in FIG. 1. The embodiment of FIG. 4 is identical with the embodiment of FIG. 1 with the single exception that a second valving means 15a and an associated liquid reservoir 18a are included in the first fluid flow circuit intermediate of capillary 12 and capillary 14. The construction of 15a is identical to that of 15. The construction of 18a is identical to that of 18. Reservoir 18a is connected to the ports of 15a in the same manner illustrated in FIG. 2. In one mode of operation of the apparatus of FIG. 4, the valving means 15a is set in its second operating position so that the solvent, after entering the valving means 15a, flows through reservor 18a before flowing into capillary 14. By operating in this mode, any minor changes in temperature which would cause a difference in pressure by expansion or contraction of the sample in liquid reservoir 18 are compensated for and offset by a compensating like expansion or contraction of the solvent in the second liquid reservoir 18a.

The sensitivity of the apparatus of FIG. 4 can be increased by initially setting valving means 15a in its first operating position, i.e., with arcuate line 41 connecting to ports 31 and 32. While the valving means is in this position, liquid reservoir 18a can be filled with a standard solution having a known viscosity. When valving means 15 is switched to its second operating position, valving means 15a also will be switched to its second operating position. When valving means 15 and 15a are both set in their second operation position, capillaries 11 and 12 both will be filled with solvent. Capillary 13 will be filled with the solution containing the solute of unknown relative viscosity which is to be determined in the experiment. At this point in time, capillary 14 will be filled with the standard solution whose viscosity is known. The pressure differential set up across the bridge and measured by differential pressure transducer 22 will measure the difference in relative viscosity of the two solutions contained in capillaries 13 and 14. The method of calculating the relative viscosity of the solute in the unknown sample will be described subsequently.

FIG. 5 illustrates another modification of the apparatus of the invention having somewhat greater flexibility in mode of operation than the embodiment illustrated in FIG. 1. The embodiment of FIG. 5 differs from the embodiment of FIG. 1 in two respects. First, a valving means 15b and an associated liquid reservoir 18b are included in line 6 intermediate of the solvent reservoir 5 and junction point 7. The connections of lines 16b and 17b to the valving means 15b are the same as shown in FIG. 2. Second, a third valving means 15c and an associated liquid reservoir 18c are included in the first circuit upstream of capillary 12. The connections of lines 16c and 17c to valving means 15c are as shown in FIG. 3.

The apparatus of FIG. 5 can be employed in the identical manner as the apparatus of FIG. 1. To employ the apparatus in this manner, valving means 15b is set in its first operating position so as to feed solvent to both of the fluid flow circuits. Similarly, valving means 15c will be set in its first operating position so as to feed only solvent to capillaries 12 and 14. Liquid reservoir 18 will be charged with sample solution in the manner previously described. Valving means 15 then will be set in its second operating position. The solvent, after flowing through capillary 11, enters liquid reservoir 18 and displaces the sample solution which then flows through capillary 13. As capillaries 11, 12, and 14 are filled with solvent, a pressure differential will be established across the bridge and will be detected by differential pressure transducer 22.

In an alternate mode of operation of the apparatus of FIG. 5, the connections of lines 16 and 17 to valving means 15 are changed to the position shown in FIG. 3. Valving means 15 and 15c are set in their second operating position. Valving means 15b is set in its first operating position and liquid reservoir 18b is filled with the sample solution. Solvent is passed through the bridge to fill capillaries 11, 13, 12, and 14 and liquid reservoirs 18 and 18c with solvent. Valving means 15b then is set to its second operating position to feed solvent into liquid reservoir 18b. The solvent displaces the sample solution which then is fed to the bridge. The sample entering the first circuit enters liquid reservoir 18c and displaces the stored solvent which then flows through capillaries 12 and 14. The sample entering the second circuit flows through capillary 11 and enters liquid reservoir 18 to displace solvent which flows through capillary 13. With solvent flowing through capillaries 12, 14, and 13 and solution flowing through capillary 11, a pressure differential will be established across the bridge and will be detected by the transducer 22.

After the viscosity of the sample has been recorded, valving means 15b is returned to its first operating position to feed solvent to the bridge. A second sample is charged to liquid reservoir 18b. Valving means 15 and 15c are set to their first operating positions so that solvent flowing through valving means 15 and 15c does not flow through the associated liquid reservoirs 18 and 18c. To rapidly flush unused sample from the liquid reservoirs, solvent is fed through port 34 and flows through arcuate line 42, port 33 and line 16 to enter the top of the liquid reservoir. This action displaces unused solution which flows through line 17, port 36, arcuate line 43 and port 35 to a waste line not shown. Valving means 15 and 15c then are returned to their second operating position and the apparatus is in a condition to measure the relative viscosity of the second sample.

The apparatus illustrated in FIG. 6 consists of two ganged bridge circuits sharing a common first fluid flow circuit. The first fluid flow circuit includes line 8 having therein, in series, first capillary 12, valving means 15a with associated liquid reservoir 18a, and second capillary 14. The first fluid flow circuit runs from junction point 7 to junction point 20. The second fluid flow circuit of the first bridge includes line 9 containing therein, in sequence in the flow stream, first capillary 11, valving means 15, and associated liquid reservoir 18, and second capillary 13. The second fluid flow circuit of the bridge runs from junction point 7 to junction point 20. Differential pressure transducer 22 measures any pressure differential existing between the first and second fluid flow circuits in the first bridge.

The second fluid flow circuit of the second bridge includes line 9a containing therein, in sequence in the flow stream, first capillary 11a, valving means 15d with its associated liquid reservoir 18d, and second capillary 13a. The second fluid flow circuit of the second bridge runs from junction point 7 to junction point 20. Transducer 22a measures any pressure differential existing between the first and second fluid flow circuits in the second bridge.

The apparatus of FIG. 6 can be operated in essentially the same manner as the apparatus of FIG. 4. Each of valving means 15, 15a, and 15d will be connected to the liquid reservoirs 18, 18a and 18d as shown in FIG. 2. Valving means 15 and 15d will be set in their first operating position and the liquid reservoirs will be filled with samples as previously described. Valving means 15a will be set in its second operating position. Solvent is fed to the two ganged bridges and fills each of capillaries 11, 13, 12, 14, 11a and 13a and liquid reservoir 18a with solvent. Valving means 15 and 15d then are set to their second operating positions. Solvent entering liquid reservoir 18 displaces stored sample solution which then flows through capillary 13. A pressure differential is detected by transtransducer 22 and recorded. Simultaneously, solvent entering liquid reservoir 18d displaces the second solution which then flows through capillary 13a. A pressure differential is detected by transducer 22a and is recorded.

To prepare the apparatus for the next analyses, either two procedures can be used. Valving means 15 and 15d can be retained in their first operating position until both transducers 22 and 22a show zero pressure differentials. This is evidence that liquid reservoirs 18 and 18d contain only solvent. The valving means then are switched to their first operating positions and the liquid reservoirs are filled with fresh samples as previously described. Alternatively, after recording the data for the first analysis, valving means 15 and 15d can be immediately switched to their first operating positions. Fresh samples then are injected into liquid reservoirs 18 and 18d. An excess of the fresh samples should be passed through the reservoirs to assure that there will be no mixing of the samples in the reservoirs.

It is noted that, as operated above, the two ganged bridges measure the samples' relative viscosities simultaneously. The average analysis time can be reduced by carrying out the analyses in sequence rather than simultaneously. In this mode of operation, valving means 15 will be switched to its second operating position as soon as liquid reservoir 18 is charged with sample. While the data for the first sample are being obtained, the operator will be charging liquid reservoir 18d with the second sample. By charging the liquid reservoirs in sequence while data are being obtained for the other sample, it is apparent that more analyses can be obtained per unit of time.

It also is apparent that a standard solution can be charged to liquid reservoir 18a. In this mode of operation, the sensitivity of the transducers can be increased as previously described with respect to the operation of the apparatus of FIG. 4.

The apparatus of FIG. 1 can be employed cooperatively with a gel permeation chromatograph (GPC) to obtain detailed information on the molecular weight distribution of a polymer. The polymer of interest will be deposited on the sorbant in the conventional manner. The sorbed polymer will be eluted with an eluting solvent. The eluant will be passed through a first detector to measure a parameter of interest, usually refractive index. The eluant then will be fed to the bridge of FIG. 1. The bridge and liquid reservoir 18 previously will have been filled with the eluting solvent. Valving means 15 will be connected to liquid reservoir 18 as shown in FIG. 3 and will be set in its second operating position. The transducer will continuously record a pressure differential as capillary 13 will continuously be filled with the eluting solvent, while the other capillaries 11, 12, and 14 will be filled with eluant. The measured pressure differential will change continuously as the molecular weight of the eluted solute polymer changes by the desorption process taking place on the gel.

FIG. 5 can be used in a similar manner by first filling both liquid reservoirs 18 and 18c with the eluting solvent. In this case, capillaries 13, 12, and 14 will be filled with solvent and capillary 11 will be filled with the eluant.

The drawings shown are schematic flow sheets which illustrate the operating principles of the apparatus of the invention. Lines 8 and 9 shown in FIGS. 1, 4, 5, and 6 are very short and in some circumstances can be dispensed with entirely. The junction point 7 can be a simple "Tee" connector which connects line 6 to capillaries 11 and 12. Similarly, junction point 20 can be a simple "Tee" connector which connects capillaries 13 and 14 to waste line 21. The fluid connection between capillary 11, port 31 of valving means 15 and line 23, can be a simple "Tee." The fluid connection between port 32 of valving means 15 and capillary 13 can be a simple line connector. The fluid connection between capillary 12, line 24, capillary 14 and pressure gauge 25 can be a simple two-line connector. As earlier noted, the pressure gauge 25 can be included at any point in the bridge upstream of either capillary 13 or 14. Its position affects the calculations and the calculations subsequently set forth are made with the gauge 25 being in the position shown in FIGS. 1, 4, 5, and 6.

Each capillary will have approximately the same length. Typically, each capillary will be about 5 feet long and have an I.D. of about 0.01 inch. As the measurement of the pressure differential is made across the bridge at points intermediate of the capillaries in each fluid flow circuit of the bridge, knowledge of the precise length of the capillaries is not required for calculation of the relative viscosity of the solute. Each set of capillaries will be selected and tested so that no pressure differential is measured when a common fluid is flowing through each of the capillaries in the bridge.

As earlier noted, the liquid reservoir(s) will be mounted in a vertical plane to assure plug flow therethrough. To minimize mixing of solvent with sample solution, the connections of the liquid reservoir to the ports of the valving means will be as shown in FIG. 2 when a sample solution is stored in the reservoir and less dense solvent is to be introduced into the top of the reservoir to displace the sample solution. When solvent is stored in the reservoir for ultimate displacement with a more dense sample solution, the connections to the valving means will be set as shown in FIG. 3 to introduce the denser sample solution in the bottom of the reservoir. Whenever it is necessary to flush residual sample solution from a liquid reservoir, it is highly desirable to introduce solvent in the top of the reservoir to avoid mixing and diluting the residual sample solution.

When the pressure gauge is positioned intermediate of the capillaries in the first fluid flow circuit, the pressure differential measured across the bridge by differential pressure transducer 22 is defined by equation 1.

$$\Delta P = P_2 - P_1$$

where:

$P_2$ is the pressure measured intermediate of the capillaries in the second fluid flow circuit, and $P_1$ is the pressure measured intermediate of the capillaries in the first fluid flow circuit.

Since $P_1$ is measured by the pressure gauge, the ratio $\Delta P/P_1$ is the complete measured quantity, we then have:

$$\frac{\Delta P}{P_1} = \left(\frac{P_2}{P_1}\right) - 1 \quad (2)$$

Poiseville's Law for pressure drop through a capillary is:

$$P = \frac{8LNQ}{r^4}$$

$$P = kN Q$$
$$P = RQ$$

Where:
- Q = flowrate
- N = viscosity
- L = length
- r = radius
- $k = (8L/r^4)$ = capillary constant
- $R = kN$ = capillary resistance When (1) solvent is present in the first fluid flow circuit and capillary 14, and (2) solution is present in the second fluid flow circuit and capillary 13, the following relationships exist:

$$P_2 = K_{13} N' Q_2 \quad (3)$$

$$P_2 = R_{13} Q_2$$

where
- $Q_2$ is the flow rate through capillaries 11 and 13,
- $N'$ is the solution viscosity, and
- $K_{13}$ is the capillary constant for capillary 13.

$$P_1 = K_{14} N_0 P_1 \quad (4)$$

$$P_1 = R_{14} Q_1$$

where:
- $Q_1$ is the flow rate through capillaries 12 and 14,
- $N_0$ is the solvent viscosity, and
- $K_{14}$ is the capillary constant for capillary 14.

It follows that:

$$\Delta P = \left(\frac{K_{13} N' Q_2}{K_{14} N_0 Q_1}\right) - 1 = \left(\frac{R_{13} Q_2}{R_{14} Q_1}\right) - 1 \quad (5)$$

Because the first and second fluid flow circuits are in parallel, the flow rate through each circuit is inversely proportional to the total capillary resistance in each circuit:

$$\frac{Q_2}{Q_1} = \frac{R_{12} + R_{14}}{R_{11} + R_{13}} = \frac{K_{12} N_0 + K_{14} N_0}{K_{11} N_0 + K_{13} N'} \quad (6)$$

Where
- $K_{12}$ is the capillary constant in capillary 12
- and $K_{11}$ is the capillary constant for capillary 11.

When $K_{11} = K_{12} = K_{13} = K_{14}$, it follows:

$$\frac{Q_2}{Q_1} = \frac{2N_0}{N' + N_0} \quad (7)$$

$$\frac{\Delta P}{P_1} = \left(\frac{N'Q_2}{N_0 Q_1}\right) - 1 \quad (8)$$

Therefore:

$$\frac{\Delta P}{P_1} = \left(\frac{2N'}{N' + N_0}\right) - 1 = \frac{N' - N_0}{N' + N_0} \quad (9)$$

When the difference between $N'$ and $N_0$ is small, the approximate relationship is defined as:

$$\frac{\Delta P}{P_1} = \frac{1}{2}\left(\frac{N' - N_0}{N_0}\right) \quad (10)$$

When a solution of known viscosity is employed as the reference viscosity in lieu of the solvent viscosity, as discussed supra with respect to FIG. 4, the calculations are somewhat different.

When a solution of known viscosity $N_2$ is charged to liquid reservoir 18a and a solution of unknown viscosity $N_1$ is charged to liquid reservoir 18, the following relationships exist $$\frac{\Delta P}{P_1} = \frac{P_2 - P_1}{P_1} = \left(\frac{P_2}{P_1}\right) - 1 \quad (11)$$

$$P_1 = KN_2 Q_1 \quad (12)$$
$$= R_1 Q_1$$

$$P_2 = KN_1 Q_2 \quad (13)$$
$$= R_2 Q_2$$

$$\frac{\Delta P}{P_1} = \left(\frac{N_1 Q_2}{N_2 Q_1}\right) - 1 \quad (14)$$

$$\frac{Q_2}{Q_1} = \frac{KN_0 + KN_1}{KN_0 + KN_2} = \frac{N_0 + N_2}{N_0 + N_1} \quad (15)$$

$$\Delta P = \left[\frac{N_1(N_0 + N_2)}{N_2(N_0 + N_1)}\right] - 1 = \frac{N_0(N_1 - N_2)}{N_2(N_1 + N_0)} \quad (16)$$

To demonstrate the capability of the apparatus of the invention, the apparatus of FIG. 4 was constructed. Each capillary was 12 ft. long and had and I.D. of 0.02 inch. The liquid reservoir was 1 ft. long, had an O.D. of 0.25" and an internal volume of 4 ml. All connection and capillaries were fabricated from stainless steel. The transducer diaphragm was rated to handle a differential pressure of 1 psi.

A polystyrene resin of known intrinsic viscosity (0.464) was dissolved in xylene to prepare a solution containing 0.20 gram/deciliter. Duplicate runs were made in one day employing a gauge pressure of 5.7 psi. The measured specific viscosity values were 0.0087 and 0.0088. The following day another set of duplicate runs were made employing a gauge pressure of 9.1 psi. The measured specific viscosity values were 0.0087 and 0.0089.

What is claimed is:

1. A capillary bridge viscometer including;
   (a) a first fluid flow circuit which is a fluid line and includes therein, in series, two capillaries;
   (b) a second fluid flow circuit which is a fluid line and includes therein, in sequence from the inlet;
      (i) a first capillary;
      (ii) a liquid reservoir having a liquid volume substantially larger than the volume of said first capillary, and including a liquid inlet and a liquid outlet in communication with the fluid line,
      (iii) a second capillary; and
      (iv) valving means intermediate the first and second capillaries which feed the liquid exiting the first capillary directly to the second capillary or into the liquid reservoir;
   (c) a fluid inlet line feeding both the first and second fluid flow circuits;
   (d) means for measuring the gauge pressure in the viscometer at any point upstream of the second capillary in either the first or second fluid flow circuit; and
   (e) means for measuring the differential pressure existing between:
      (i) a point intermediate of the capillaries in the first fluid flow circuit, and
      (ii) a point intermediate of the capillaries in the second fluid flow circuit; the viscometer being further characterized in that the lengths and diameters of the capillaries are such that essentially no pressure differential is established between the fluid flow circuits when a common fluid is flowing through all of the capillaries.

2. A capillary bridge viscometer of claim 1 in which:
   (a) all of the fluid lines in the fluid flow circuits have substantially identical internal diameters; and
   (b) all of the capillaries in the fluid flow circuits have substantially identical internal diameters and lengths.

3. A capillary bridge viscometer of claim 2 in which the liquid reservoir in the second fluid flow circuit includes a vertically aligned cylindrical chamber whose diameter is larger than the diameter of the fluid lines in the second fluid flow circuit.

4. A capillary bridge viscometer of claim 2 in which the first fluid flow circuit is identical in construction to the second fluid flow circuit.

5. A capillary bridge viscometer of claim 2 which includes means for feeding fluid from alternate sources to the fluid inlet line of the viscometer.

6. A capillary bridge viscometer of claim 5 in which the means for feeding liquid from alternate sources to the fluid inlet line includes:
   (a) a first liquid reservoir in communication with said fluid inlet line;
   (b) a second liquid reservoir, downstream of said first liquid reservoir, having a volume substantially larger than the capillaries present in the fluid flow circuits and including a liquid inlet and a liquid outlet in communication with the fluid inlet line; and
   (c) valving means which feed liquid from the first liquid reservoir directly to the two fluid flow circuits or feed liquid from the first liquid reservoir into the second liquid reservoir.

7. A capillary bridge viscometer of claim 2 in which the first fluid flow circuit includes therein, upstream of the first capillary;

(a) a liquid reservoir having a liquid volume substantially larger than the capillaries included in said first fluid flow circuit and including a liquid inlet and a liquid outlet in communication with the fluid line, and (b) valving means which feed fluid from the fluid inlet line directly to the inlet of the first capillary or feed liquid from the fluid inlet line into the liquid reservoir.

8. A capillary bridge viscometer of claim 7 in which the liquid reservoir included in the first fluid flow circuit includes a vertically aligned cylindrical chamber whose diameter is larger than the diameter of the fluid lines in the first fluid flow circuit.

9. A capillary bridge viscometer of claim 2 which includes;

(a) a third fluid flow circuit which is identical in construction to the second fluid flow circuit;

(b) a fluid inlet line feeding each of the three fluid flow circuits;

(c) means for measuring the gauge pressure in the viscometer at any point upstream of the second capillary in any of the fluid flow circuits;

(d) means for measuring the differential pressure existing between;
  (i) a point intermediate of the capillaries in the first fluid flow circuit, and
  (ii) a point intermediate of the capillaries in the second fluid flow circuit; and (e) means for measuring the differential pressure existing between:
  (i) a point intermediate of the capillaries in the third fluid flow circuit, and
  (ii) a point intermediate of the capillaries in the first fluid flow circuit;

the viscometer being further characterized in that:

(f) all of the fluid lines in the fluid flow circuits have substantially identical internal diameters; and (g) all of the capillaries in the fluid flow circuits have substantially identical internal diameters and lengths.

10. A capillary bridge viscometer of claim 9 in which the construction of the first fluid flow circuit is identical to the construction of the second and third fluid flow circuit.

11. A process for measuring the relative viscosity of a solute in solution with a solvent for said solute consisting essentially of;

(a) feeding solvent through a first fluid flow circuit containing two capillaries in series;

(b) feeding solvent through a second fluid flow circuit containing, in sequence from the inlet;
  (i) a first capillary,
  (ii) a liquid reservoir having a liquid volume substantially larger than the volume of said first capillary, and
  (iii) a second capillary;

(c) continuing feed of solvent through the two fluid flow circuits until they are filled with solvent;

(d) subsequent to step (c), feeding a solution of solute in said solvent to the first and second fluid flow circuits to:
  (i) fill both capillaries of the first fluid flow circuit with said solution,
  (ii) fill the first capillary of said second fluid flow circuit with said solution, and
  (iii) feed solution exiting the first capillary of the second fluid flow circuit into the liquid reservoir of the second fluid flow circuit and thereby displace pure solvent stored in the liquid reservoir and feed said displaced pure solvent through the second capillary; and (e) during step (d);
  (i) measuring the gauge pressure in the viscometer at any point upstream of the second capillary in either the first or second fluid flow circuit, and
  (ii) measuring the differential pressure existing between a point intermediate of the first and second capillaries in the first fluid flow circuit and a point intermediate of the first and second capillaries of the second fluid flow circuit.

12. A process of claim 11 in which:

(a) the first fluid flow circuit contains, upstream of the first capillary, a liquid reservoir substantially identical to the liquid reservoir included in the second fluid flow circuit;

(b) sufficient solvent is fed to both fluid flow circuits to fill each of the capillaries and the liquid reservoirs in the two fluid flow circuits, (c) subsequent to step (b) a solution of solute in said solvent is fed to both fluid flow circuits to;
  (i) feed said solution into the liquid reservoir of the first fluid flow circuit and thereby displace pure solvent stored in said reservoir and feed said displaced pure solvent through the two capillaries of said circuit, and (ii) feed solution exiting the first capillary of the second fluid flow circuit into the liquid reservoir of the second fluid flow circuit and thereby displace pure solvent stored in the liquid reservoir and feed displaced pure solvent through the second capillary of the second fluid flow circuit; and (d) during step (c);
  (i) the gauge pressure in the viscometer is measured at any point upstream of the second capillary in either the first or second fluid flow circuit, and
  (ii) the differential pressure existing between a point intermediate of the first and second capillaries in the first fluid flow circuit and a point intermediate of the first and second capillaries of second fluid flow circuit is measured.

13. A process for measuring the relative viscosity of a solute in solution with a solvent for said solvent for said solute consisting essentially of;

(a) feeding solvent through a first fluid flow circuit containing two capillaries in series thereby filling both capillaries with solvent;

(b) feeding solvent through a second fluid flow circuit containing, in sequence from the inlet;
  (i) a first capillary,
  (ii) a liquid reservoir having a liquid volume substantially larger than the volume of said first capillary, and filled with a solution of solute in said solvent, and
  (iii) a second capillary;

thereby filling the first capillary with solvent, feeding solvent into the liquid reservoir, thereby displacing solution stored in the liquid reservoir and feeding said displaced solution through the second capillary; and (c) during step (b);
  (i) measuring the gauge pressure in the viscometer at any point upstream of the second capillary in either the first or second fluid flow circuit, and (ii) measuring the differential pressure existing between a point intermediate of the first and second capillaries in the first fluid flow circuit and a point intermediate of the first and second capillaries of the second fluid flow circuit.

14. A process of claim 13 in which;
(a) both fluid flow circuits contain, in sequence from the inlet;
  (i) a first capillary,
  (ii) a liquid reservoir having a liquid volume substantially larger than the volume of said first capillary, and filled with a solution of solute in said solvent, and
  (iii) a second capillary;
(b) the liquid reservoir in the first fluid flow circuit contains a first solution of solute in said solvent;
(c) the liquid reservoir in the second fluid flow circuit contains a second solution of solute in said solvent; and
(d) the second capillary of the first fluid circuit contains the first solution of said solute when the second capillary of the second fluid flow circuit contains the second solution of said solute.

15. A process for independently measuring two parameters of multiple fractions of a solvent soluble polymer which consists essentially of;
(a) depositing fractions of a solvent soluble polymer on a gel permeation chromatographic column;
(b) eluting said polymer from the column of (a) with an eluting solvent;
(c) feeding the eluant of (b) through a first detector which continuously measures a property indicative of a solute polymer property;
(d) continuously feeding the eluant exiting the first detector to a capillaary bridge viscometer including,
  (i) a first fluid flow circuit containing two capillaries in series, said first circuit being filled with eluting solvent;
  (ii) a second fluid flow circuit containing, in sequence from the inlet,
    (aa) a first capillary,
    (bb) a liquid reservoir having a liquid volume substantially larger than the volume of the said first capillary, and
    (cc) a second capillary, liquid reservoir said second circuit being filled with eluting solvent; and
(e) during step (d);
  (i) measuring the guage pressure in the viscometer at any point upstream of the second capillary in either the first or second fluid flow circuit, and
  (ii) measuring the differential pressure existing between a point intermediate of the first and second capillaries in the first fluid flow circuit and a point intermediate of the first and second capillaries of the second fluid flow circuit.

16. A capillary bridge viscometer of claim 1 in which the valving means is a two-position, multi-port valve characterized in that it includes a series of fluid lines adapted to connect each port to one adjacent port when the valve is in its first operating position and to connect each port to its second adjacent port when the valve is in its second operating position.

17. A capillary bridge viscometer of claim 16 in which, when the valving means is set in an operating position to feed liquid from the first capillary to the second capillary, the valving means also includes a fluid path to feed a second fluid to the liquid reservoir.

18. A capillary bridge viscometer of claim 17 in which the liquid reservoir in the second fluid flow circuit includes a vertically aligned cyclindrical chamber whose diameter is larger than the diameter of the fluid lines in the second fluid flow circuit.

* * * * *